(12) United States Patent
Ladet

(10) Patent No.: US 9,795,717 B2
(45) Date of Patent: Oct. 24, 2017

(54) ENZYMATICALLY DEGRADABLE COMPOSITIONS

(75) Inventor: Sébastien Ladet, Lyons (FR)

(73) Assignee: Sofradim Production, Trevoux (FR)

( * ) Notice: Subject to any disclaimer, the term of this patent is extended or adjusted under 35 U.S.C. 154(b) by 606 days.

(21) Appl. No.: 14/005,831

(22) PCT Filed: Mar. 23, 2012

(86) PCT No.: PCT/IB2012/000806
§ 371 (c)(1),
(2), (4) Date: Sep. 18, 2013

(87) PCT Pub. No.: WO2012/127328
PCT Pub. Date: Sep. 27, 2012

(65) Prior Publication Data
US 2014/0013998 A1    Jan. 16, 2014

Related U.S. Application Data

(60) Provisional application No. 61/467,109, filed on Mar. 24, 2011.

(51) Int. Cl.
| | |
|---|---|
| *C08L 5/08* | (2006.01) |
| *A61L 31/04* | (2006.01) |
| *C08J 3/075* | (2006.01) |
| *C08J 3/24* | (2006.01) |
| *C08L 5/10* | (2006.01) |
| *C08L 71/02* | (2006.01) |
| *C08B 37/08* | (2006.01) |
| *A61L 27/18* | (2006.01) |
| *A61L 27/52* | (2006.01) |
| *A61L 27/58* | (2006.01) |
| *C08G 65/333* | (2006.01) |

(52) U.S. Cl.
CPC ............ *A61L 31/041* (2013.01); *A61L 27/18* (2013.01); *A61L 27/52* (2013.01); *A61L 27/58* (2013.01); *C08B 37/003* (2013.01); *C08G 65/33337* (2013.01); *C08J 3/075* (2013.01); *C08J 3/246* (2013.01); *C08L 5/08* (2013.01); *C08L 5/10* (2013.01); *C08L 71/02* (2013.01); *C08J 2305/08* (2013.01); *C08J 2371/02* (2013.01)

(58) Field of Classification Search
CPC ........ A61L 31/041; A61L 27/18; A61L 27/52; A61L 27/58; C08B 37/003
USPC ...................................................... 106/162.2
See application file for complete search history.

(56) References Cited

U.S. PATENT DOCUMENTS

| | | | |
|---|---|---|---|
| 5,412,083 A * | 5/1995 | Giese et al. ................... 536/20 |
| 2003/0129730 A1 | 7/2003 | Chenite et al. | |
| 2009/0068250 A1 | 3/2009 | Gravagna et al. | |
| 2009/0275489 A1* | 11/2009 | Kilaas .................... C09K 8/565 |
| | | | 507/209 |
| 2011/0320009 A1* | 12/2011 | Ladet et al. ............... 623/23.72 |

FOREIGN PATENT DOCUMENTS

| | | | | |
|---|---|---|---|---|
| AU | 2009305114 A1 * | 5/2011 | | |
| FR | WO 2010043978 A2 * | 4/2010 | ............ | A61L 27/48 |
| WO | 2010043978 A2 | 4/2010 | | |
| WO | WO 2010/095044 A2 | 8/2010 | | |

OTHER PUBLICATIONS

International Search Report for PCT/IB12/00806 date of completion is Jul. 5, 2012 (3 pages).

Sei-Ichi Aiba: "Studies on Chitosan.\Reactivity of Partially N-Acetylated Chitosan in Aqueous Media", Makromolekulare Chemie, Huthig und WEPF Verlag, Basel, CH, vol. 194, No. 1, Jan. 1, 1993, pp. 65-75, XP000334528, ISSN: 0025-116X, DOI: 10.1002/MACP. 1993. 021940105 p. 67, paragraph 2; figure 3; table 1.

European Communication dated Oct. 1, 2015 in corresponding European Patent Application No. EP 12720955, 4 pages.

* cited by examiner

*Primary Examiner* — Alexander Polyansky

(57) ABSTRACT

Enzymatically degradable compositions containing biocompatible polymers reactive with glycosaminoglycan compositions having a first glycosaminoglycan compound having a first degree of acetylation and a second glycosaminoglycan compound having a second degree acetylation different than the first degree of acetylation.

20 Claims, No Drawings

ENZYMATICALLY DEGRADABLE COMPOSITIONS

CROSS-REFERENCE TO RELATED APPLICATIONS

This application is a National Stage Application of PCT/IB12/00806 under 35USC §371 (a), which claims benefit of and priority to U.S. Provisional Patent Application Ser. No. 61/467,109 filed Mar. 24, 2011, the disclosures of each of the above-identified applications are hereby incorporated by reference in their entirety.

BACKGROUND

Technical Field

The present disclosure relates to enzymatically degradable compositions including at least one synthetic biocompatible polymer having reactive electrophilic groups which are capable of reacting with a combination of glycosaminoglycans having different degrees of acetylation, and use thereof as precursors in forming biocompatible polymers and/or degradable hydrogels.

Background of Related Art

The use of medical gels such as hydrogels can be advantageous due to the physicochemical properties of the hydrogels. Hydrogels typically have excellent compatibility with human and animal tissue. Physically cross-linked hydrogels can withstand attack by body fluids, blood, urine and other bodily secretions without significant damage. Many hydrogels may be non-adherent to tissue, lack an affinity for binding to proteins and fail to allow for cell adsorption. Hydrogels may also be non-thrombogenic. These characteristics make some hydrogels suitable for use in surgical procedures, e.g., for prevention of adhesions after surgery. The ability of some hydrogels to act as bulking agents has been utilized in connection with treatment of gastro-esophageal reflux disease (GERD), urinary incontinence, fecal incontinence and sterilization of mammals. Hydrogels may also be used to create a matrix in the treatment of damaged cartilage.

Poly(ethylene glycol) (PEG), a hydrophilic polymer that exhibits acceptable toxicity, and immunogenicity has found great utility in biotechnology, specifically, in forming hydrogels. PEG is generally considered to be biocompatible and is not immunogenic, which is to say that PEG is generally capable of coexistence with living tissues and does not tend to produce an immune response in the body. However, conventional hydrogels and other medical implants based on PEG and other synthetic biocompatible polymers may be susceptible to in-vivo degradation, generally induced by hydrolysis of specific linkages of the polymer chains (e.g., ester linkages). Thus, such degradation profiles may be considered passive, since degradation primarily occurs due to the presence of water. It would be desirable to provide a hydrogel formed from PEG derivatives or other synthetic biocompatible polymers that may be suitable for in-vivo enzymatic degradation.

SUMMARY

The present disclosure provides for compositions including a synthetic biocompatible polymer having reactive electrophilic groups, and a glycosaminoglycan composition including a first glycosaminoglycan compound having a first degree of acetylation and a second glycosaminoglycan compound having a second degree of acetylation, wherein the first degree of acetylation is different than the second degree of acetylation.

The present disclosure further provides for hydrogels including a first precursor having a first enzymatic degradation profile and a second precursor having a second enzymatic degradation profile different than the first enzymatic degradation profile. The first precursor may be an activated or functionalized poly(ethylene glycol) polymer and the second precursor may be any compound having a free amino group and having a tunable in-vivo enzymatic degradation profile. In some embodiments, the second precursor may be a glycosaminoglycan composition having a first glycosaminoglycan compound having a first degree of acetylation and a second glycosaminoglycan compound having a second degree of acetylation that is higher than the first degree of acetylation.

In certain embodiments, the second precursor may be a chitosan composition having a first chitosan compound having a first degree of acetylation and a second chitosan compound having a second degree of acetylation that is higher than the first degree of acetylation.

Compositions of the present disclosure may also include a chitosan composition bonded to a functionalized poly(ethylene glycol), wherein the chitosan composition includes a first chitosan compound having a first degree of acetylation and a second chitosan compound having a second degree acetylation higher than the first degree of acetylation.

In other embodiments, methods of making the compositions described herein may include combining a chitosan composition and functionalized poly(ethylene glycol), wherein the chitosan composition includes a first chitosan compound having a first degree of acetylation and a second chitosan compound having a second degree acetylation higher than the first degree of acetylation.

In further embodiments, a hydrogel of the present disclosure may include a chitosan composition bonded to a functionalized poly(ethylene glycol) having at least one electrophilic group, wherein the chitosan composition includes a first chitosan compound having a first degree of acetylation and at least two free amine groups and a second chitosan compound having a second degree acetylation higher than the first degree of acetylation and at least two free amine groups.

A first aspect of the invention is a composition comprising a biocompatible polymer including pendant electrophilic groups; and a glycosaminoglycan composition including a first glycosaminoglycan compound having a first degree of acetylation and a second glycosaminoglycan compound having a second degree acetylation different than the first degree of acetylation.

Another aspect of the invention is a method of making a composition comprising combining a glycosaminoglycan composition and a biocompatible polymer having pendant electrophilic groups, wherein the glycosaminoglycan composition includes a first glycosaminoglycan compound having a first degree of acetylation and a second glycosaminoglycan compound having a second degree acetylation different than the first degree of acetylation.

In embodiments, the biocompatible polymer comprises a poly(ethylene glycol) functionalized to include pendant electrophilic groups.

In embodiments, the biocompatible polymer comprises electrophilic groups selected from the group consisting of N-hydroxysuccinimide ester (NHS), N-hydroxysulfosuccinimide ester (SNHS), N-hydroxyethoxylated succinimide ester (ENHS) and combinations thereof.

In embodiments, the first glycosaminoglycan compound is selected from the group consisting of hyaluronic acid, chondroitin, dermatan, chitin, chitosan, keratan, heparin, and derivatives and combinations thereof.

In embodiments, the second glycosaminoglycan compound is selected from the group consisting of hyaluronic acid, chondroitin, dermatan, chitin, chitosan, keratan, heparin, and derivatives and combinations thereof.

In embodiments, the first and second glycosaminoglycan compounds comprise the same glycosaminoglycan compound. For example, the first glycosaminoglycan compound is a first chitosan compound, and the second glycosaminoglycan compound is a second chitosan compound.

In embodiments, the first and second glycosaminoglycan compounds comprise different glycosaminoglycan compounds.

In embodiments, the first glycosaminoglycan compound comprises a degree of acetylation of about 1% to about 10%.

In embodiments, the second glycosaminoglycan compound comprises a degree of acetylation of about 10% to about 70%.

Another aspect of the invention is a composition comprising:
a chitosan composition bonded to a functionalized poly(ethylene glycol), wherein the chitosan composition includes a first chitosan compound having a first degree of acetylation and a second chitosan compound having a second degree acetylation higher than the first degree of acetylation.

Another aspect of the invention is a method of making a composition comprising combining a chitosan composition and functionalized poly(ethylene glycol), wherein the chitosan composition includes a first chitosan compound having a first degree of acetylation and a second chitosan compound having a second degree acetylation higher than the first degree of acetylation.

In embodiments, the functionalized poly(ethylene glycol) includes at least one electrophilic functional group.

In embodiments, the at least one electrophilic functional group is selected from the group consisting of N-hydroxysuccinimide ester (NHS), N-hydroxysulfosuccinimide ester (SNHS), and N-hydroxyethoxylated succinimide ester (ENHS).

In embodiments, the first chitosan compound comprises a degree of acetylation of about 1% to about 10%.

In embodiments, the second chitosan compound comprises a degree of acetylation of about 10% to about 70%.

In embodiments, the first and second chitosan compounds have a molecular weight of about 1,000 g/mol to about 10,000 g/mol.

In embodiments, each of the first and second chitosan compounds has at least two free amine groups.

Another aspect of the invention is a hydrogel comprising a composition as described above.

DETAILED DESCRIPTION

The degradable compositions described herein include at least one biocompatible polymer and a combination of glycosaminoglycan compounds having different degrees of acetylation. The degradable compositions may be susceptible to hydrolysis and/or enzymatic degradation. In some embodiments, the degradable compositions include a combination of glycosaminoglycan compounds having different degrees of acetylation which are susceptible to varying degrees of enzymatic degradation. In some embodiments, the degradable compositions include biocompatible polymers susceptible to hydrolysis.

The biocompatible polymers described herein may be natural or synthetic and may include electrophilic reactive groups capable of interacting with the free amino groups found in the combination of glycosaminoglycan compounds of varying degrees of acetylation to form bonds. In certain embodiments, the glycosaminoglycan compounds may be combined with at least one synthetic biocompatible polymer having pendant electrophilic groups.

Synthetic biocompatible polymer includes any oligomer or polymer that is not naturally occurring and/or is produced via chemical synthesis or modification. Examples of suitable synthetic biocompatible polymers may include any biocompatible polymer which has been chemically modified to include electrophilic reactive groups and derivatives of such polymers. In addition, natural biopolymers which have been modified, such as to include degradable linkages, and/or functionalized to include electrophilic reactive groups may also be suitable examples of synthetic biocompatible polymers.

The biocompatible polymers may be absorbable, non-absorbable, hydrophilic, hydrophobic and combinations thereof. The biocompatible polymers may also be linear, branched, star-shaped, dendrimetic and the like. In embodiments, the synthetic biocompatible polymer is poly(ethylene glycol) or a derivative of poly(ethylene glycol).

Poly(ethylene glycol) and derivatives thereof in accordance with the present disclosure are capable of reacting with the glycosaminoglycan compositions to form a bond therewith. The PEG derivatives described herein may be functionalized or activated PEG derivates that are substantially non-toxic and should not produce undesirable effects.

As used herein the terms "group," "functional group," and/or "reactive group," may all be somewhat synonymous in the chemical arts and may be used in the art and herein to refer to distinct, definable portions or units of a molecule or polymer and to units that perform some function or activity and may be reactive with other molecules or polymers.

As used herein the term "linkage" is used to refer to groups that may be formed as the result of a chemical reaction and typically may be covalent linkages. Hydrolytically stable linkages mean that the linkages may be stable in water and do not react with water at useful pHs for an extended period of time, potentially indefinitely. Hydrolytically unstable linkages may be those that react with water, typically causing a molecule to separate into two or more components. A linkage is said to be hydrolysable if the linkage is susceptible to hydrolysis.

In embodiments, the synthetic biocompatible polymers according to the present disclosure include at least two pendant electrophilic functional groups capable of reacting with free amine groups on the first and/or second glycosaminoglycan compounds. The synthetic biocompatible polymers may include a multifunctional core, with one more than one arms each having a pendant or terminal electrophilic functional group capable of reacting with the free amines on the first and/or second glycosaminoglycan compounds. It should be understood that only one arm may be attached to the core which includes a terminal functional group capable of reacting with an amine group, with no other groups attached to the core or with non-reactive arms attached to the core. The other arms may, for example, be simple —OH terminated PEG arms or PEG-based arms terminated with reactive groups that are not amine-reactive. In embodiments, the present synthetic biocompatible polymers may include anywhere from 1 to 8 arms that include a terminal functional group capable of reacting with an amine group on the first and second glycosaminoglycan compounds.

The functional group may be an electrophilic functional group. Some examples of electrophilic groups capable of reacting with the glycosaminoglycan compositions include, but are not limited to, N-hydroxysuccinimide ester (NHS), N-hydroxysulfosuccinimide ester (SNHS), and N-hydroxyethoxylated succinimide ester (ENHS).

The advantage of the NHS-amine reaction may be that the reaction kinetics leads to quick gelation usually within about 10 minutes, in embodiments from about 10 seconds to about 1 minute. This fast gelation is particularly useful for in situ reactions on live tissue. The NHS-amine crosslinking reaction leads to formation of N-hydroxysuccinimide as a side product. The sulfonated or ethoxylated forms of N-hydroxysuccinimide may be useful due to their increased solubility in water and hence their rapid clearance from the body. The sulfonic acid salt on the succinimide ring does not alter the reactivity of NHS group with the primary amines.

A biocompatible polymer functionalized to include pendant electrophilic groups, such as a multi-arm poly(ethylene glycol) including pendant-NHS groups, may be combined with a glycosaminoglycan composition containing free amine groups to form a crosslinked polymer. In embodiments, the glycosaminoglycan composition includes more than one amine group and essentially serves as a crosslinker. Generally, any combination of glycosaminoglycan compounds having free amine groups may be used to form a glycosaminoglycan composition suitable for interacting with the synthetic biocompatible polymers described herein.

The resulting crosslinked polymer may include hydrolysable and non-hydrolysable portions. More specifically, the resulting hydrogel or polymer may contain hydrolysable portions found in the biocompatible polymer which may be susceptible to passive degradation by the exposure of aqueous fluids. The resulting hydrogel or polymer may also contain non-hydrolysable portions in the glycosaminoglycan portions which may be susceptible to a less passive and/or more controllable degradation process such as enzymatic degradation, wherein the varying degrees of acetylation of the multiple glycosaminoglycan compounds may be varied to increase or decrease the hydrogel or polymers degradation time (also known as the in-vivo persistence).

In terms of degradation of the resulting synthetic biocompatible polymer/glycosaminoglycan composition hydrogel or polymer, while not wishing to be bound by any theory, it is believed that the varying degrees of acetylation of the glycosaminoglycans provides the hydrogel or polymer with varying degrees of in-vivo persistence. As a result, the in-vivo persistence of the resulting crosslinked polymers may be dependent upon or controlled by the degree of acetylation of the glycosaminoglycan compounds.

The glycosaminoglycan compositions may include any combination of various glycosaminoglycan compounds having different degrees of acetylation. Glycosaminoglycan compounds are long-branched polysaccharides which contain repeating disaccharide units having various amounts of pendant acetylated amines. Depending upon the degree of acetylation, some portion of the pendant amines will not be acetylated, leaving that portion reactive with electrophilic groups on the synthetic biocompatible polymer.

Any suitable glycosaminoglycan compound having free amine groups may used to form the compositions described herein. The free amine groups being able to interact with the electrophilic groups of the biocompatible polymers to form a covalent bond or cross-link. Some non-limiting examples of suitable glycosaminoglycans include hyaluronic acid, chondroitin, dermatan, chitin, chitosan, keratan, heparin, and derivatives and combinations thereof. In some embodiments, the glycosaminoglycan composition may include two or more of the same glycosaminoglycan compounds wherein the glycosaminoglycan compounds include different varying degrees of acetylation. For example, in some embodiments, the glycosaminoglycan composition includes at least two chitosan compounds of varying degrees of acetylation.

Chitosan is a natural linear co-polymer of N-acetyl D-glucosamine (acetylated unit) and D-glucosamine (non-acetylated unit). Chitosan may be produced by partial or full deacetylation of chitin. Chitin may be extracted from natural sources, e.g., squid pens, exoskeletons of crustaceans such as shrimp shells, or vegetable sources such as mushrooms, e.g. "champignon de Paris." Chitosan may also be synthetically produced or synthesized by modified microorganisms such as bacteria.

The structure of native chitosan provides viscoelastic properties as well as specific interactions with biological substrates that may not be found in other modified polysaccharides, such as polysaccharides in which the —$NH_2$ group would be chemically added. Chitosan, then, may provide good viscosity for use as an adhesive and be biologically accepted.

The adhesion of chitosan with other polymers includes the association of different kinds of interactions, such as electrostatic interactions, hydrogen bonds, and hydrophobic interactions, to name a few. Chitosan, under certain circumstances, is a cationic polymer containing $NH_3^+$ groups. The positively charged primary amino groups of chitosan attract anionic groups of other polymers. Thus, chitosan and anionic polymers are able to form polyelectrolyte complexes. Polyelectrolyte complex formation may improve the mechanical properties of the polymers and lead to new structures, such as precipitates, films, fibers, and gels.

Adhesion of chitosan with other polymers may also be promoted by reinforcing the mechanical properties of the formulation by creating covalent bonds between both the components of the adhesive formulation and with the substrate. Chitosan has $NH_2$ groups which can react covalently with electrophilic groups, such as those discussed above.

Even though the interaction between the glycosaminoglycan compounds and the synthetic biocompatible polymers may be due to covalent bonding, the importance of physical gelation due to the behavior of the glycosaminoglycan under physiological conditions cannot be neglected. For example, interactions between chitosan and other functionalized biopolymers, such as oxidized starch, have been studied by FTIR, NMR, and rheology. Covalent bonds exist between the two polymers, but it may coexist with other types of interactions such as hydrogen bonding or hydrophobic interactions.

The degree of acetylation (DA), or the percentage of N-acetyl D-glucosamine, in the glycosaminoglycan compounds may be from about 0% to about 80%. In embodiments, the degree of acetylation may be from about 0% to about 10%. Low DA's ensure that sufficient amounts of $NH_3^+$ are available to generate ionic interactions. The degree of acetylation also ensures that the glycosaminoglycan has the capability, (e.g., free amino groups), to be crosslinked with a functionalized synthetic polymer. The glycosaminoglycan compound may have a molecular weight from about 1,000 g/mol to about 10,000 g/mol. In embodiments, glycosaminoglycan a molecular weight of about 2,000 g/mol to about 9,000 g/mol.

The glycosaminoglycan composition may include a mixture of glycosaminoglycan compounds in any physical form. In some embodiments, the glycosaminoglycan composition may be in a dry particulate form, i.e., a powder or granule. In other embodiments, the glycosaminoglycan composition may be a solution. For example, a solution of two chitosan compounds having different degrees of acetylation may be prepared by dissolving the two chitosan compounds in distilled water with a stoechiometric amount of HCl to ensure the complete protonation of all $NH_2$ groups. The final solution may contain about 0.5% (w/w) to about 20% (w/w) chitosan.

The glycosaminoglycan solution may be in a liquid, viscous form and placed in a syringe for immediate or later use. The solution of glycosaminoglycans may also be directly coated on a support or implant, such as a mesh. The mesh may be prepared by soaking in the glycosaminoglycan solution and drying the coated mesh in an oven or in a laminar flow hood. In embodiments, the process may be repeated several times to ensure a proper coating displaying the required adhesive properties for the selected indication of use, e.g., fixation of extra peritoneal or retroperitoneal meshes, skin flap closure, etc.

In embodiments, the glycosaminoglycan composition may include two different chitosan compounds having different degrees of acetylation. The first chitosan compound may have a relatively low DA, which may be from about 0% to about 10%, in embodiments from about 1% to about 2%. The second chitosan compound may have a higher DA than the DA of the first chitosan compound. The DA of the second chitosan compound may be from about 10% to about 80%, in embodiments, from about 15% to about 70%. The chitosan content of the glycosaminoglycan composition may include: a) from about 70% to about 100% of the first chitosan compound, in embodiments, from about 80% to about 95% of the first chitosan compound; and b) from about 0% to about 30% of the second chitosan compound, in embodiments, from about 5% to about 20% of the second chitosan compound. Without being bound any particular theory, it is believed that the combination of low and high DA chitosan compounds modifies the balance between hydrophilic and hydrophobic interactions of the chitosan content of the composition, which leads to an increase in adhesion.

In embodiments, a chitosan composition including a first chitosan compound having a first degree of acetylation and a second chitosan compound having a second degree acetylation higher than the first degree of acetylation may be combined with a functionalized or activated synthetic biocompatible polymer having at least one electrophilic group to form various compositions, such as adhesive, hydrogels and the like. The ratio of the chitosan composition to the synthetic biocompatible polymer may be adjusted to provide a desired formulation. Each formulation is characterized by its mix ratio (MR). As used herein, the term "mix ratio" means the amount of free amine groups of chitosan over the amount of electrophilic groups of the functionalized synthetic biocompatible polymer. The mix ratio may be at least about 1, in embodiments from about 1 to about 40. Further, the chitosan content of the chitosan composition may be adjusted to achieve a desired strength and/or degradation profile of the resulting adhesive. In other words, adjusting the total degree of acetylation by combining two or more chitosan compounds having different degrees of acetylation provides for fine tuning of the degradation profile of the resulting composition. In embodiments, each component of the composition may be diluted with a buffer prior to use for pH adjustment.

As noted above, the synthetic biocompatible polymer, i.e., a PEG derivative, may include multiple arms wherein each arm includes a pendant NHS group which may be reactive with a glycosaminoglycan composition having varying degrees of acetylation. In embodiments, the combination of the number of pendant NHS groups in the biocompatible polymer and the number of pendant amine groups in the glycosaminoglycan composition may total greater than or equal to 5 to form a cross-linkable hydrogel. A glycosaminoglycan composition including two or more glycosaminoglycan compounds which includes at least 2 or more pendant amine groups may be combined with a multi-arm biocompatible polymer having at least two arms to form a cross-linked hydrogel suitable for use as a tissue-sealant, adhesion barrier, hemostat or tissue-filler. Of course, any combination of pendant NHS and amines totaling 5 or more may be suitable for forming suitable cross-linked hydrogels.

The synthetic biocompatible polymers, i.e., degradable poly(ethylene glycol) derivatives, described herein may combined with a glycosaminoglycan composition to form any implantable material including, but not limited to tissue sealants, adhesives, hemostats, coatings on a medical device, drug delivery devices, adhesion-barriers, and/or tissue-fillers. In embodiments, the composition forms a biodegradable hydrogel material suitable for implantation. The composition may be applied directly to tissue or may be applied to a surface of an implantable medical device, such as a stent, mesh, suture, staple, balloon, suture anchor, bone plate, pin, screw, rod, and the like. The composition may be applied to the tissue or medical device using any suitable method including, but not limited to, dipping, wiping, brushing, spraying, injecting, and pouring and the like.

Several biocompatible crosslinked hydrogels may be produced using the synthetic biocompatible polymers and glycosaminoglycan compositions described herein. The reaction conditions for crosslinking will depend on the nature of the functional groups. In embodiments, the reactions may be conducted in buffered aqueous solutions at pH 5 to 12. Suitable non-limiting examples of buffers may include sodium borate, triethanol amine, sodium phosphate, carbonate, and potassium hydrogen phthalate. Elevated pH may increase the speed of the reactions. In some embodiments, organic solvents such as ethanol or isopropanol may be added to improve the reaction speed or to adjust the viscosity of a given formulation.

In embodiments, the at least one of the synthetic biocompatible polymers and glycosaminoglycan compositions may be in particulate form. In such embodiments, the cross-linking reaction may not occur until at least one of the two compounds is exposed to moisture or bodily fluids. In some embodiments, the particulate materials may be applied separately or sequentially to a medical device or on living tissue. In other embodiments, the particulate materials may be applied simultaneously to a medical device or tissue. Examples of suitable medical devices the biocompatible polymer and the glycosaminoglycan compositions can be combined with include implantable devices such as sutures, meshes, catheters, cables, sternum closures, clips, pins, foams, films, adhesion barriers, slings, stents, pledgets, buttresses and the like.

Without being bound by any theory, it is believed the crosslinked hydrogels described above degrade due to hydrolysis of the ester linkage in the biocompatible polymer and enzymatic degradation of the inner amide bond in the acetylated glycosaminoglycan. Aqueous solutions of the synthetic biocompatible polymers and glycosaminoglycan compositions described herein may be made just before the crosslinking reaction due to reaction of NHS groups with water. Longer "pot life" may be obtained by keeping these solutions at lower pH (e.g., from about 4 pH to about 5 pH).

The crosslinking density of the resultant biocompatible crosslinked polymer may be controlled by the overall molecular weight of the synthetic biocompatible polymers and glycosaminoglycan compositions and the number of functional groups available per molecule. A lower molecular weight between crosslinks such as 600 will give much higher crosslinking density as compared to a higher molecular weight such as 10,000. In embodiments, higher molecular weight synthetic biocompatible polymers may be used. In some embodiments, synthetic biocompatible polymers of more than 3000 may be used so as to obtain elastic gels.

In embodiments, the biocompatible crosslinked polymers of this invention may be formed "in situ" at a surgical site in the body. The various methodologies and devices for performing "in situ" gelation, developed for other adhesive or sealant systems such fibrin glue or sealant applications, may be used with the biocompatible crosslinked polymers of this invention. Thus, in one embodiment, an aqueous solution of a glycosaminoglycan composition (e.g. chitosan composition including a two chitosan compounds having different degrees of acetylation) and a synthetic biocompatible polymer having reactive electrophilic groups (PEG derivative polymer terminated with multiple NHS end groups) are co-sprayed on to tissue using an air assisted sprayer such that the two fluid streams mix in the air and at the site of application to form a crosslinked biodegradable hydrogel that is capable of adhering to tissue within seconds. The two solutions may be applied simultaneously or sequentially. In some embodiments, it is preferred to apply the precursor solutions sequentially so as to "prime" the tissue, resulting in improved adherence of the biocompatible crosslinked polymer to the tissue. Where the tissue is primed, the biocompatible polymer may be applied to the tissue first, followed by the glycosaminoglycan composition.

One may use specialized devices to apply the two compounds, such as an adhesive sprayer or such as those described in U.S. Pat. Nos. 4,874,368; 4,631,055; 4,735,616; 4,359,049; 4,978,336; 5,116,315; 4,902,281; 4,932,942; Published PCT Patent Application No. WO 91/09641; and R. A. Tange, "Fibrin Sealant" in *Operative Medicine: Otolaryngology*, volume 1 (1986), the disclosures of which are herein incorporated by reference.

In embodiments, the synthetic biocompatible polymers and glycosaminoglycan compositions described herein may be stored and sterilized in separate containers to prevent premature cross-linking from occurring. In some embodiments, the synthetic biocompatible polymers and glycosaminoglycan compositions described herein may be stored and sterilized in the same container wherein the cross-linking is prevented from occurring by the use of buffers.

It is envisioned that kits for delivering the materials to the site of implantation may be designed. The kits may include a first composition which includes at least one of the synthetic biocompatible polymers described herein and a second composition which includes at least one of the glycosaminoglycan compositions described herein. The first and second compositions may be stored in the same or separate container(s) and the kit includes a means for delivering the first and second compositions to the site of implantation and/or the site of application on a medical device. Suitable delivery devices include, but are not meant to be limited to, one or more surgical syringes, double-barrel syringes, or the specialized devices described above, i.e., an adhesive sprayer. Mixture of the materials which form the cross-linked hydrogels described herein may occur immediately prior to, during or after implantation.

In embodiments, at least one bioactive agent may be included in the degradable compositions described herein. The agents may be freely admixed with the components of the degradable compositions or may be tethered to the components through any variety of chemical bonds. In these embodiments, the degradable compositions can also serve as a vehicle for delivery of the bioactive agent. The term "bioactive agent" as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be added to the degradable compositions in any suitable form of matter, e.g., powders, liquids, gels, and the like.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; anti-histamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factors, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Bioactive agents can also be additives, such as fucans, emulsifiers, surfactants, humectants, buffering agents, pH modulators, chelating agents, viscosity agents, and any other product which may enhance tissue repair, limit the risk of sepsis, and modulate mechanical properties of the degradable compositions. It is envisioned that metal ions known for their bioactivity in favor of tissue regeneration may also be used.

It will be understood that various modifications may be made to the embodiments disclosed herein. For example, the adhesion strength may be influenced by modifying the degree of acetylation of chitosan and/or the molar mass of chitosan. Therefore, the above description should not be construed as limiting, but merely as an exemplification of the embodiments. Those skilled in the art will envision other modifications within the scope and spirit of the present disclosure. Such modifications and variations are intended to come within the scope of the following claims.

What is claimed is:

1. A composition comprising:
   a mixture including polyethylene glycol functionalized to include pendant electrophilic groups; and
   a glycosaminoglycan composition including a first glycosaminoglycan compound having a first degree of acetylation and a second glycosaminoglycan compound having a second degree acetylation different than the first degree of acetylation,
   wherein the pendant electrophilic groups are selected from the group consisting of N-hydroxysuccinimide ester (NHS), N-hydroxysulfosuccinimide ester (SNHS), N-hydroxyethoxylated succinimide ester (ENHS) and combinations thereof.

2. The composition of claim 1, wherein the first glycosaminoglycan compound is selected from the group consisting of hyaluronic acid, chondroitin, dermatan, chitin, chitosan, keratan, heparin, and derivatives and combinations thereof.

3. The composition of claim 1, wherein the second glycosaminoglycan compound is selected from the group consisting of hyaluronic acid, chondroitin, dermatan, chitin, chitosan, keratan, heparin, and derivatives and combinations thereof.

4. The composition of claim 2, wherein the first glycosaminoglycan compound is chitosan.

5. The composition of claim 3, wherein the second glycosaminoglycan compound is chitosan.

6. The composition of claim 1, wherein the first and second glycosaminoglycan compounds comprise different glycosaminoglycan compounds.

7. The composition according to claim 1, wherein the first glycosaminoglycan compound comprises a degree of acetylation of about 1% to about 10%.

8. The composition according to claim 1, wherein the second glycosaminoglycan compound comprises a degree of acetylation of about 10% to about 70%.

9. A method of making the composition of claim 1 comprising mixing a glycosaminoglycan composition and a polyethylene glycol functionalized to include pendant electrophilic groups, wherein the glycosaminoglycan composition includes a first glycosaminoglycan compound having a first degree of acetylation and a second glycosaminoglycan compound having a second degree acetylation different than the first degree of acetylation.

10. The method of claim 9, wherein the first glycosaminoglycan compound is selected from the group consisting of hyaluronic acid, chondroitin, dermatan, chitin, chitosan, keratan, heparin, and derivatives and combinations thereof.

11. The method of claim 9, wherein the second glycosaminoglycan compound is selected from the group consisting of hyaluronic acid, chondroitin, dermatan, chitin, chitosan, keratan, heparin, and derivatives and combinations thereof.

12. The method of claim 9, wherein the first and second glycosaminoglycan compounds comprise the same glycosaminoglycan compound.

13. The method of claim 9, wherein the first and second glycosaminoglycan compounds comprise different glycosaminoglycan compounds.

14. The method of claim 9, wherein the first glycosaminoglycan compound comprises a degree of acetylation of about 1% to about 10%.

15. The method of claim 9, wherein the second glycosaminoglycan compound comprises a degree of acetylation of about 10% to about 70%.

16. The method of claim 10, wherein the first glycosaminoglycan compound is chitosan.

17. The method of claim 11, wherein the second glycosaminoglycan compound is chitosan.

18. The composition of claim 1, wherein the glycosaminoglycan composition includes about 80% to about 95% of the first glycosaminoglycan compound and about 5% to about 20% of the second glycosaminoglycan compound, and the second degree acetylation of the second glycosaminoglycan compound is higher than the first degree of acetylation of the first glycosaminoglycan compound.

19. The composition of claim 11, wherein the first glycosaminoglycan compound is chitosan and the second glycosaminoglycan compound is chitosan.

20. The composition of claim 19, wherein the chitosan of the first glycosaminoglycan compound comprises a degree of acetylation of about 0% to about 10% and the chitosan of the second glycosaminoglycan compound comprises a degree of acetylation of about 15% to about 70%.

* * * * *